US006152728A

United States Patent [19]

Griffel

[11] Patent Number: 6,152,728

[45] Date of Patent: Nov. 28, 2000

[54] COMBINED DRIP PREVENTING AND FRAGRANCE DISPENSING CANDLE HOLDER

[75] Inventor: Giora Griffel, Bergenfield, N.J.

[73] Assignee: The Candle Machine Co., Tenafly, N.J.

[21] Appl. No.: 09/217,921

[22] Filed: Dec. 21, 1998

Related U.S. Application Data

[63] Continuation-in-part of application No. 09/095,997, Jun. 11, 1998, Pat. No. 5,879,152.

[51] Int. Cl.$^{7}$ .............................. A61L 9/03; A61L 9/02; F23D 3/16; F21S 13/12

[52] U.S. Cl. .......................... 431/293; 431/289; 431/292; 362/447; 362/96; 362/161; 422/125

[58] Field of Search .................................... 431/292, 293, 431/289, 290; 362/293, 161, 447, 162, 163, 171, 172, 173, 174, 176, 180, 181, 182, 101, 312, 313, 314, 84, 96; 422/125, 126, 305; 239/34

[56] References Cited

U.S. PATENT DOCUMENTS

| | | | |
|---|---|---|---|
| 84,103 | 11/1868 | Faote . | |
| D. 288,722 | 3/1987 | Harada | D20/11 |
| 945,963 | 1/1910 | Lang | 362/447 |
| 964,841 | 7/1910 | Berau | 431/293 |
| 1,175,057 | 3/1916 | Goeddertz . | |
| 1,200,121 | 10/1916 | Knapp . | |
| 1,255,614 | 2/1918 | Knapp . | |
| 1,365,485 | 11/1921 | Guest . | |
| 2,254,906 | 9/1941 | Petrulis | 431/289 |
| 2,503,236 | 4/1950 | Churchill | 431/293 |
| 3,071,952 | 1/1963 | Churchill . | |
| 3,767,910 | 10/1973 | Stratton | 240/10 B |
| 3,958,917 | 5/1976 | Naz | 431/289 |
| 4,493,011 | 1/1985 | Spector | 362/96 |
| 4,544,351 | 10/1985 | Marsicano | 431/288 |
| 4,566,055 | 1/1986 | Klees | 362/162 |
| 4,579,717 | 4/1986 | Gyulay | 422/125 |
| 4,755,135 | 7/1988 | Kwok | 431/291 |
| 5,057,005 | 10/1991 | Kwok | 431/253 |
| 5,197,454 | 3/1993 | Lee | 126/9 R |
| 5,827,483 | 10/1998 | Fullam | 422/122 |
| 5,879,152 | 3/1999 | Griffel | 431/293 |
| 5,911,955 | 6/1999 | Fullam | 422/125 |

FOREIGN PATENT DOCUMENTS

| | | | |
|---|---|---|---|
| 1280056 | 11/1961 | France | 431/293 |
| 2721519 | 12/1995 | France . | |
| 3001359 | 7/1981 | Germany . | |
| 9-16517 | 6/1997 | Japan . | |
| 230229 | 3/1925 | United Kingdom | 431/293 |
| 2067739 | 7/1981 | United Kingdom . | |
| 3287 | 2/1989 | United Kingdom | 431/293 |

*Primary Examiner*—Carl D. Price
*Attorney, Agent, or Firm*—Robert W. J. Usher

[57] ABSTRACT

A fragrance dispensing device has a candle follower with an annular shoulder portion for sitting on a shoulder of the candle to descend under gravity during consumption thereof maintaining the reservoir at a constant distance from the candle flame throughout burning. The candle follower can be formed at an upper end with a bowl having inner and outer walls forming inner and outer compartments receiving melted wax and volatile fragrance, respectively. The inner wall portion can be annular, extending substantially concentrically within the outer wall or, in another embodiment, there are two, semicircular, inner wall portions formed on diametrically opposite sides of the outer wall portion defining therewith respective fragrance oil containing compartments. In other examples, the reservoir is supported above the candle flame by vertically sliding rods or sleeves carried by the candle follower or is an annular dish seated on the upper edge of the bowl.

19 Claims, 11 Drawing Sheets

COMBINED DRIP PREVENTING AND FRAGRANCE DISPENSING CANDLE HOLDER

RELATED APPLICATION

This is a continuation-in-part application of Ser. No 09/095,997, filed Jun. 11, 1998 issued as U.S. Pat. No. 5,879,152 on Mar. 9, 1999.

FIELD OF THE INVENTION

The invention relates to a combined drip preventing and fragrance dispensing candle holder.

BACKGROUND OF THE INVENTION

The problems associated with dripping candles, complete burning and effective candle mounting are well recognized and there have been numerous attempts, over more than one hundred years, to provide both practical and aesthetically attractive solutions. There have also been numerous prior attempts to utilize the heat of the candle flame to vaporize fragrances, to perfume a room.

One type of a drip preventing candle holder is taught by U.S. Pat. No. 1,365,485 issued in 1921 to Guest and comprises a drip preventing and candle stabilizing cap member or follower having an annular shoulder portion for sitting on a shoulder of the candle to descend under gravity during consumption thereof and a central, wick receiving opening with a lip to contain melted wax and a cylindrical skirt depending from the annular portion; a stand having a base and an upstanding, socket-less candlestick with a candle supporting surface and receivable in sealing engagement within the cap during the last stages of consumption of the candle to reduce or prevent leakage of melted wax; and complementary cap guiding means on the cap member and base.

In the Guest patent, the candlestick is of constant width, substantially equal to the width of the candle and supporting surface and, preferably, the guiding means includes a cylindrical sleeve member upstanding from the base of the stand surrounding the candlestick in coaxial relation to provide therebetween a skirt receiving socket. The skirt is of greater axial length than the candle and is guided by sliding receipt in the socket during burning, ensuring even, vertical descent of the cap member. Furthermore, the lip is extended to provide a large bowl as necessary to contain the increased amount of wax melted as a result of the high thermal conductivity of the cap which is apparently metal.

However, that construction is relatively bulky and heavy, also requiring vent holes at an upper end for cooling the candle body and another set of holes at the edge of the socket extending into the bowl to drain back reliquified wax from the bowl at the final stage of burning adding to complexity and manufacturing cost. Removal of any wax leaking into the socket can be relatively time consuming and difficult.

In addition, as with another proposal taught by G.B patent 230,229 granted 1925 to Riley, in which a follower's skirt telescopically receives the candlestick, the candle body is concealed from view substantially completely throughout burning as the follower is made of metal.

Prior proposals to vaporize selected fragrances by utilizing the heat from a candle flame are taught by U.S. Pat. No. 5,197,454 issued 1993 to Lee; U.S. Pat. No. 4,781,895 issued 1988 to Spector; U.S. Pat. No. 5,827,483 issued 1998 to Fullam; and U.S. Pat. No. 3,958,917 issued 1976 to Naz.

The patents to Lee, Spector and Fullam, teach that the liquid fragrance is contained in a bowl which is supported above the candle flame by a frame. However, the additional frameworks are relatively bulky and cumbersome, multipart constructions, which maintain the fragrance containing bowl at a constant vertical height and do not automatically adjust the height of the bowl to the changing height of the candle flame during consumption of the candle which can result in differential heating and correspondingly different rates of fragrance vaporization and distribution.

Other prior candle holders with cap members or followers, some of which are made of transparent glass are taught by U.S. Pat. Nos. 84,103; 1,225,614; 1,350,461; 1,671,652; 2,503,236; 3,071,952; 3,767,910; 4,544,357; 4,566,055; 4,755,135; 5,057,005; U.S. Pat. No. design 288,722; U.K. patent application publication 2,067,739 and Japanese patent application publication 9161517.

SUMMARY OF THE INVENTION

It is one object of the invention to provide a combined drip preventing and fragrance dispensing candle holder or device which operates effectively to ensure leak free consumption and relatively even fragrance evaporation while also permitting use of a generic candle.

Another object of the invention is to provide such holder or device which permits the candle body and flame to be seen throughout burning.

A further object of the invention is to provide such holder or device that permit use of the candle flame to vaporize fragrances.

A still further object of the invention is to provide such holder or device that can be easily cleaned.

An additional object of the invention is to provide such holder or device which is of relatively simple construction suitable for economic production by conventional mass production techniques.

Accordingly, the invention provides a drip preventing device of the type described above in which the candle follower incorporates a compartment providing a reservoir of fragrance which is volatile when heated. As the follower maintains the reservoir at the same position in relation to the candle flame throughout consumption of the candle, the heating effect and vaporization rate are relatively constant ensuring that the fragrance is dispensed relatively evenly over time.

More specifically, the invention provides a combined drip preventing and fragrance dispensing device comprising a drip preventing device for a candle of a type comprising a candle follower having an annular shoulder portion for sitting on a shoulder of the candle to descend under gravity during consumption thereof and a central, wick receiving opening with an annular lip and a cylindrical skirt depending from the annular shoulder portion for receiving a candle body; wherein the candle follower is one piece of transparent material and is formed at an upper end with a bowl comprising an outer wall portion flaring outwardly and upwardly from the annular lip and an inner wall portion joined to the outer wall portion, thereby dividing the bowl into inner and outer compartments, for containing melted candle wax and fragrance oil, respectively.

In one embodiment, the inner wall portion is annular, extending substantially concentrically within the outer wall so that the liquid fragrance receiving compartment is annular and surrounds the inner compartment for melted wax to ensure even heating of the fragrance. In another embodiment, there are two or more, semicircular, inner wall portions formed on diametrically opposite sides of the outer wall portion defining therewith respective fragrance oil containing compartments.

Preferably, the liquid fragrance receiving compartments are imperforate and the inner walls join the outer wall at a mid point thereof so that the outer, liquid fragrance containing compartments are at a higher level than the melted wax and the inner wall portions incline inwardly as they extend upward facilitating heating of the liquid fragrance therein.

The device further comprises a stand having a base and an upstanding, socket-less candlestick with a recessed candle supporting surface and the skirt of the follower is elongate for containing an entire candle and so that the candlestick is receivable in sliding engagement within the skirt, guiding descent of the cap member throughout the entire burning of the candle and for sealing engagement within the cap member during a final stage of consumption to prevent leakage of melted wax.

This construction will provide sufficient lateral support and guidance for the cap throughout descent to enable both the essentially socketless structure to be maintained with total, drip-free consumption of a universally available, generic candle type with some thickness variation accommodated.

Substantially the entire candle is exposed to view throughout burning maintaining the desired natural and symbolic quality of the living flame which is the primary reason for candle use in homes and restaurants while also dispensing a selected fragrance in an aesthetically acceptable manner and only while the candle is burning.

BRIEF DESCRIPTION OF THE DRAWINGS

Specific embodiments of the invention will now be described by way of example only with reference to the accompanying drawings in which.

DESCRIPTION OF PARTICULAR EMBODIMENTS

Figure 1:
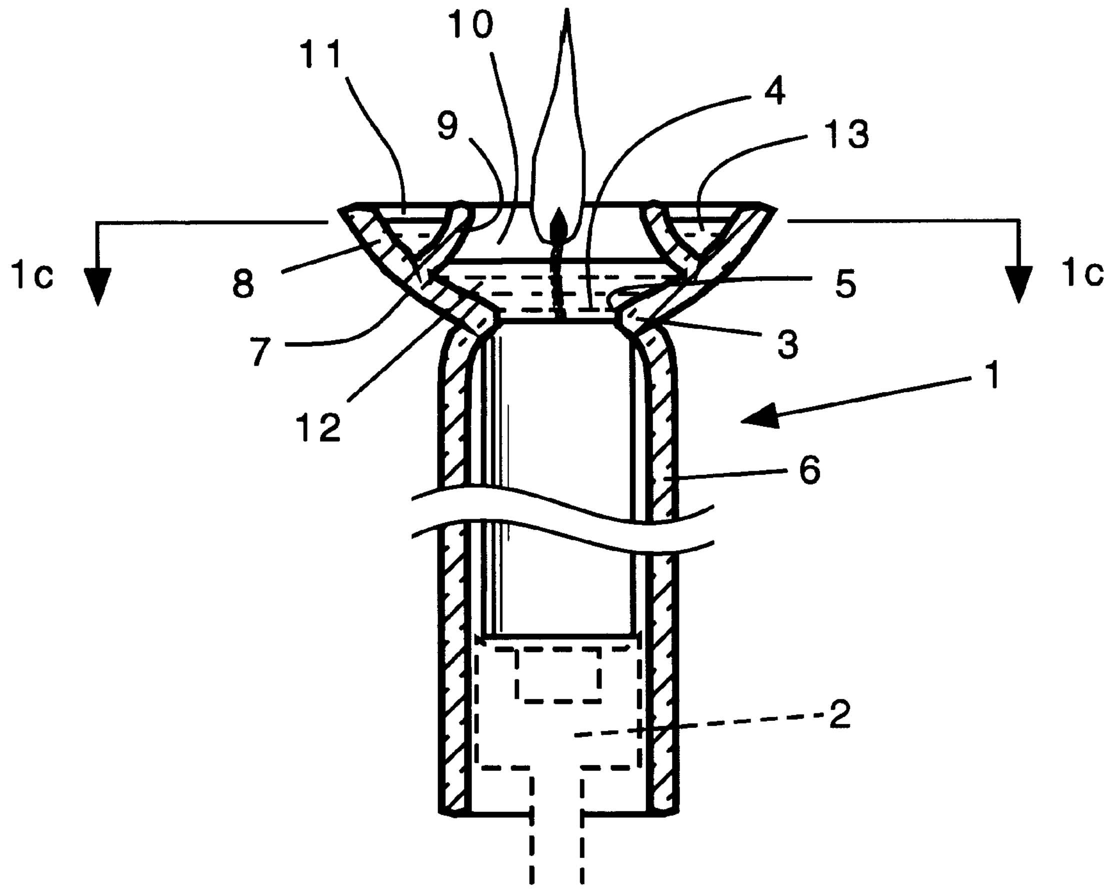
FIG. 1*a* is a schematic, axial cross-sectional view of a first embodiment of a combined drip preventing and fragrance dispensing device with the candle partly consumed.
FIG. 1*b* is perspective view, partly cut away, of the first embodiment.
FIG. 1*c* is a schematic cross-sectional view of the first embodiment taken along line 1*c*—1*c* of FIG. 1*a;*
Figure 1:
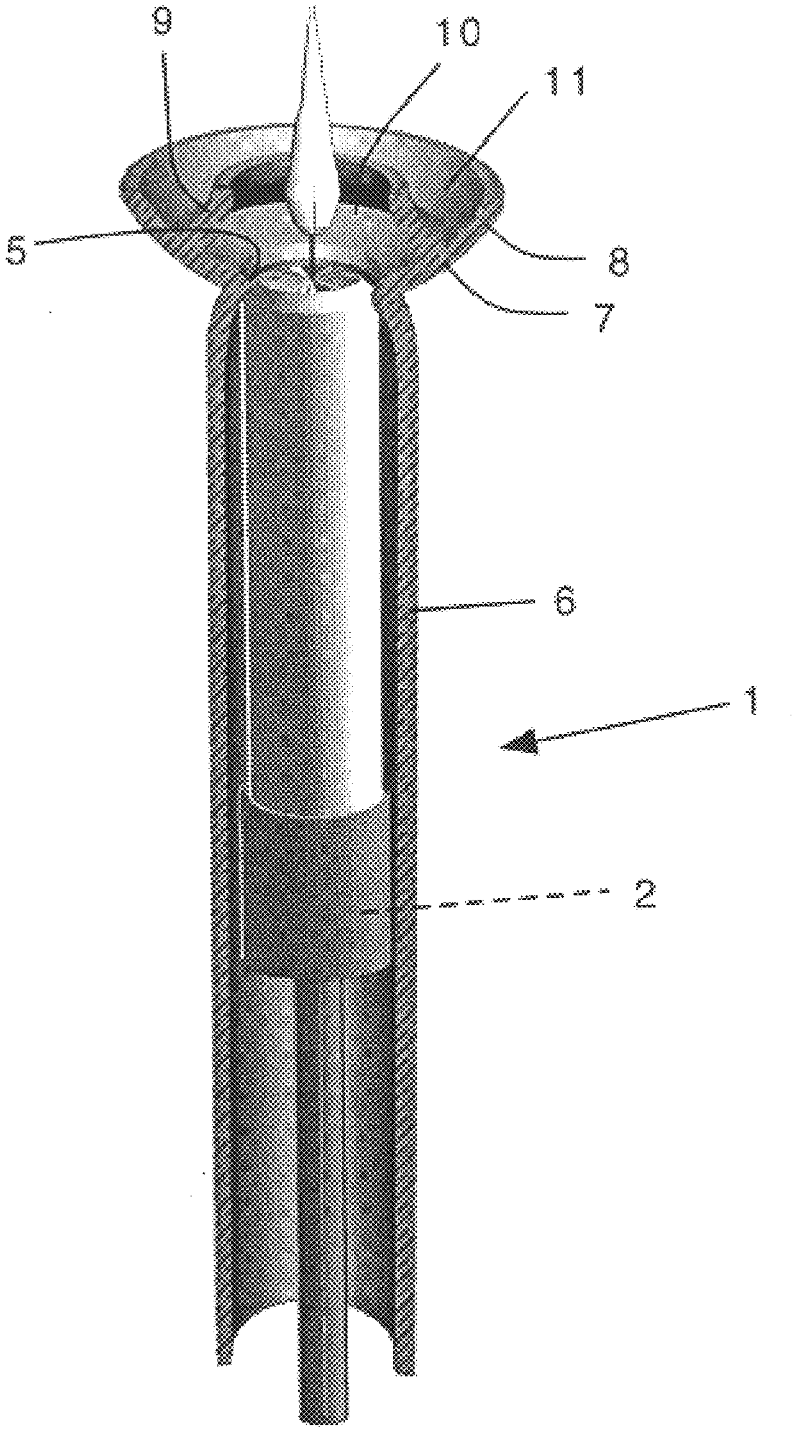
Figure 1:
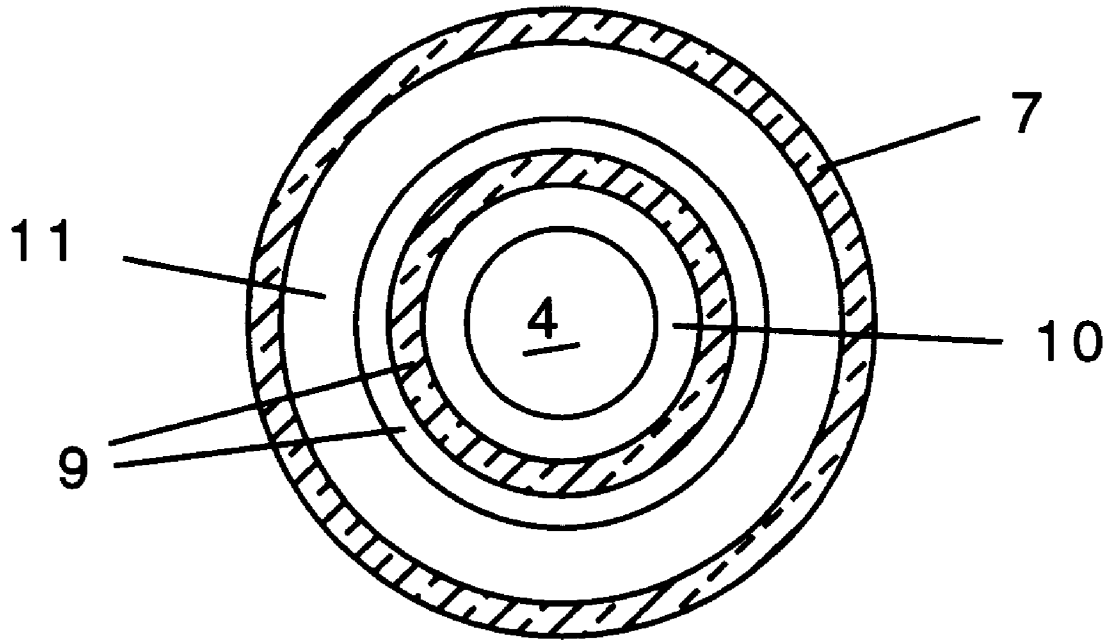

The first embodiment of the invention, shown in FIGS. 1*a*, 1*b* and 1*c*, comprises a drip preventing and candle stabilizing cap member or follower 1 with a reservoir of volatile liquid fragrance 11 and candlestick 2.

The cap member 1 is made in one piece of heat resistant, transparent glass and has an annular shoulder or constriction 3 for sitting on an upper shoulder of the candle formed with a central, wick receiving opening 4 with an annular lip 5. A skirt 6 depends from the annular shoulder 3, spaced from, and longer than, the candle body. A bowl 7 is formed by an outer wall portion 8 flaring outwardly and upwardly from the annular lip 5 and an inner wall portion 9 is joined to the outer wall portion 8 dividing the bowl into an inner compartment 10 and an outer, imperforate, compartment 11, respectively, for containing, respectively, melted candle wax 12 and liquid fragrance 13 for vaporization by heat from the candle. The inner wall portion 9 is annular, extending substantially concentrically within the outer wall portion 8 so that the outer compartment or reservoir 11 for liquid fragrance surrounds the inner compartment and is at a constant distance from the candle flame for a substantially even heating effect.

The inner wall portion 9 joins the outer wall portion 8 at a mid point thereof so that the outer, liquid fragrance containing compartment 11 is normally at a higher level than the melted wax 12 and the inner wall portion 9 inclines inwardly as it extends upward facilitating heating of the liquid fragrance therein.

As the position of follower relative to the flame remains constant throughout consumption of the candle, the heating effect and vaporization rate also remain relatively constant, ensuring that the fragrance is dispensed relatively evenly, over time.

As will be understood, the stand has a candle supporting surface which is at least as wide as the candle and is received by the skirt as a sliding fit.

Figure 2:
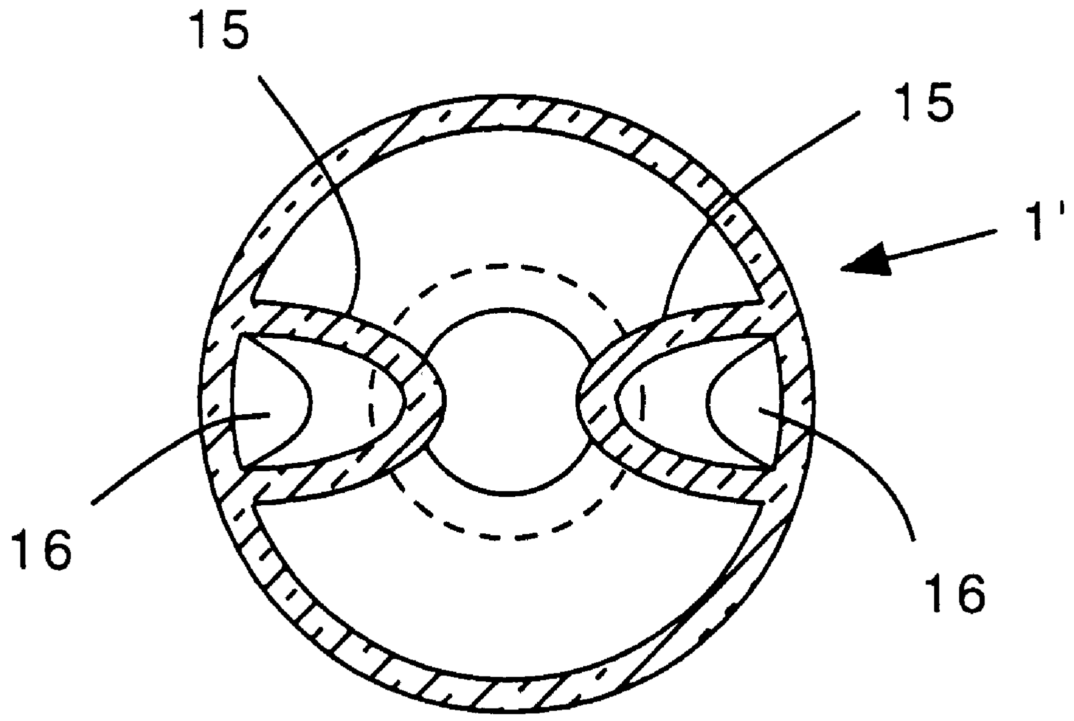
FIG. 2 is a similar cross-sectional view to that of FIG. 1*c* showing a second embodiment.

The second embodiment shown in FIG. 2, differs from the first embodiment only in that inner wall portion is not annular but comprises two, semicircular, inner wall parts 15 formed on diametrically opposite sides of the outer wall portion 8' defining therewith two imperforate fragrance containing compartments or reservoirs 16 providing a relatively larger melted wax receiving compartment. An advantage of this embodiment is that different fragrances may be heated simultaneously in respective compartments.

Figure 3:
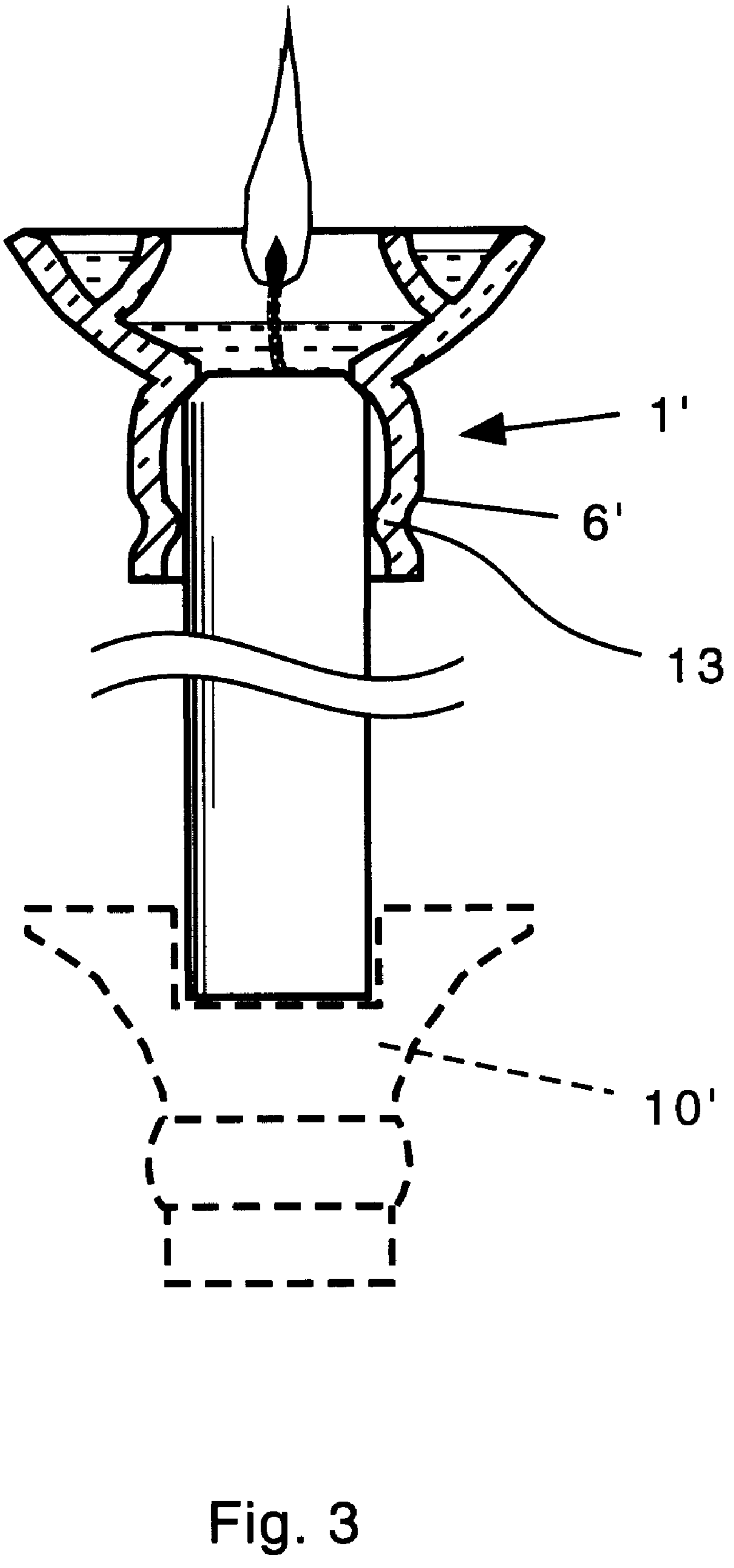
FIG. 3 is a schematic axial cross-sectional view of a third embodiment of the invention.

In the third embodiment shown in FIG. 3, the cap member or candle follower 1' is of similar construction to that of either of the prior embodiments except that the skirt 6' is shorter so that it does not receive the candlestick 10'. A ring of individual radially inwardly extending, candle engaging, protruberences 13 are formed around the skirt adjacent a lower end thereof to obviate tilting through descent which otherwise could prevent descent of the candle follower.

Figure 4:
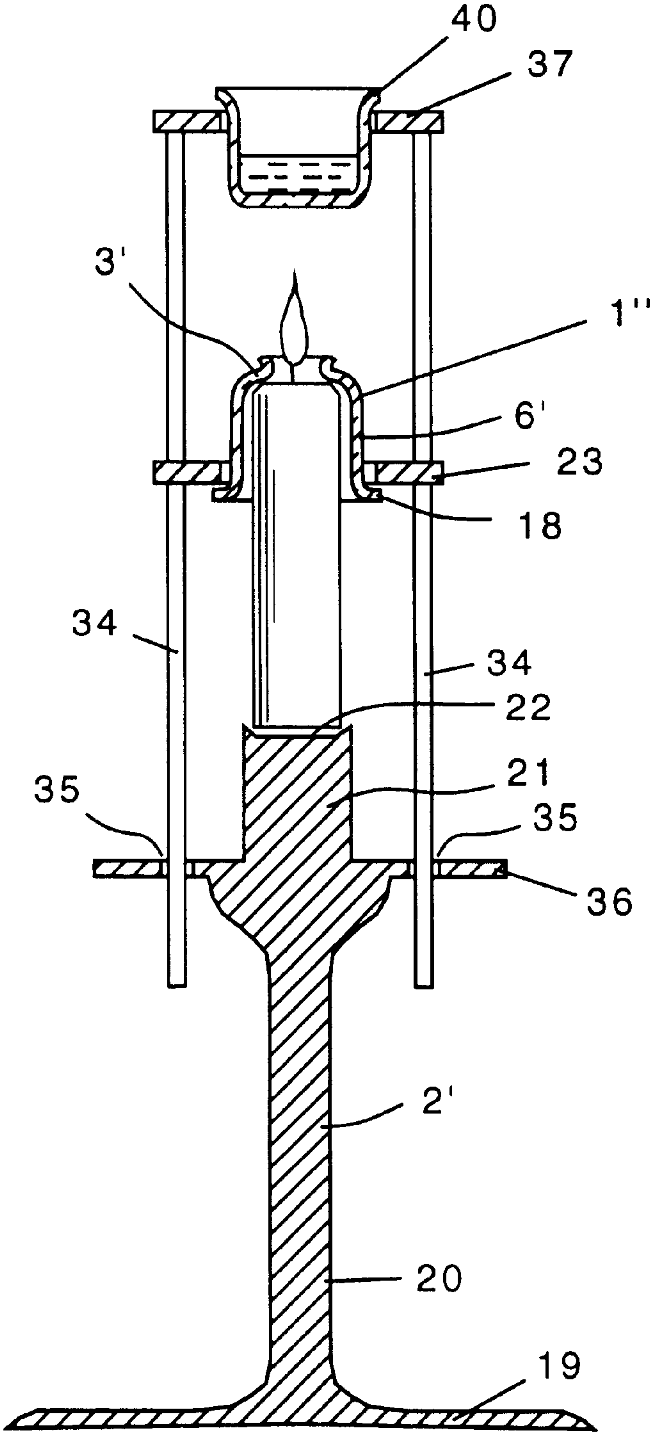
FIG. 4*a* is an elevational view, partly in cross-section of a fourth embodiment of socketless drip preventing and fragrance dispensing candle holder with the candle partly consumed.
FIG. 4*b* is a similar view to FIG. 4*a* but at a final stage of consumption of the candle.
Figure 4:
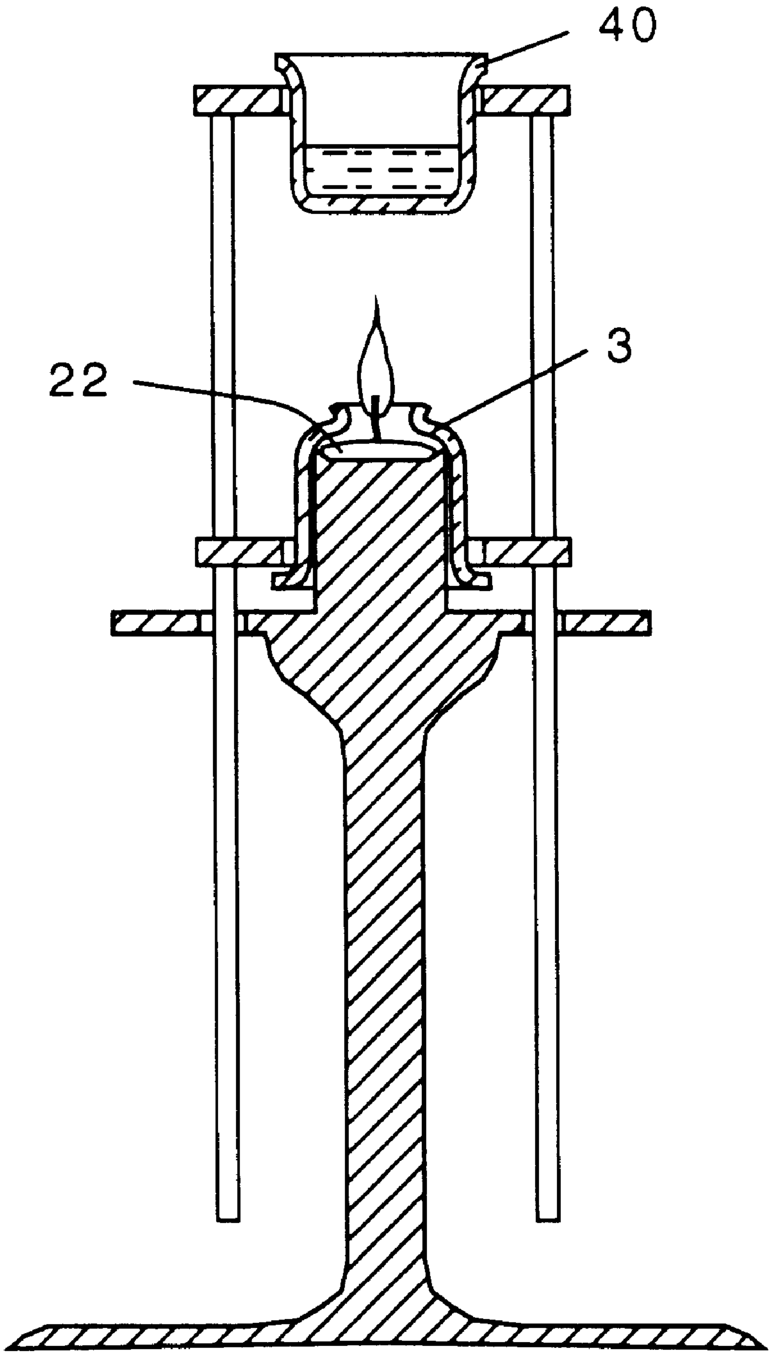

In the fourth embodiment shown in FIGS. 4*a* and 4*b*, a lower portion of the skirt 6' of the cap member or candle follower 1" extends outwardly forming a radially outwardly flared edge portion 18.

The stand 2' has a base 19 and an upstanding socket-less candlestick 20 with a shallow concave candle supporting surface 22 at least as wide as the candle.

A cap member or candle follower guiding assembly comprises a metal annulus 23 which sits on the portion 18 of the skirt 6' so as to extend around the candle, spaced radially outwardly therefrom and carries metal guide rods 34 in depending relation which are slidingly received in respective guide rod receiving sockets 35 located in a circular bearing member 36 provided on the stand at a sufficient height above the base 19 to permit full descent of the cap member. A portion 21 of the candlestick upstands above the bearing member 36 a distance at least equal to the height of the skirt 6', enabling the cap to descend sufficiently to bring the shoulder 3' into sealing engagement with the periphery of the candle supporting surface, as described in the above-mentioned parent patent application. Upward extensions of the guide rods 34 from the annulus 23 providing support rods for a further annulus 37 on their upper ends which support a glass bowl 40 or reservoir of volatile liquid fragrance aligned above the candle flame for warming by the candle. Thus, the reservoir is essentially carried by the candle follower.

In operation, sliding receipt of the guide rods in the sockets maintains the entire cap member on a fixed vertical axis throughout gravitation down the candle body throughout total consumption while maintaining the bowl at a constant distance above the candle to ensure even heating and evaporation of the fragrance throughout consumption of the candle. As indicated in FIG. 4*b*, at the end of the descent, the cap member comes to rest with the candle supporting surface in sealing engagement with the annular shoulder adjacent the aperture so that the resulting enclosure is sufficiently shallow to permit total consumption of the candle while preventing leakage of melted wax pooling in the concavity while the bowl remains at the same height above the candle before consumption, as shown in FIG. 4*a*.

Figure 5:
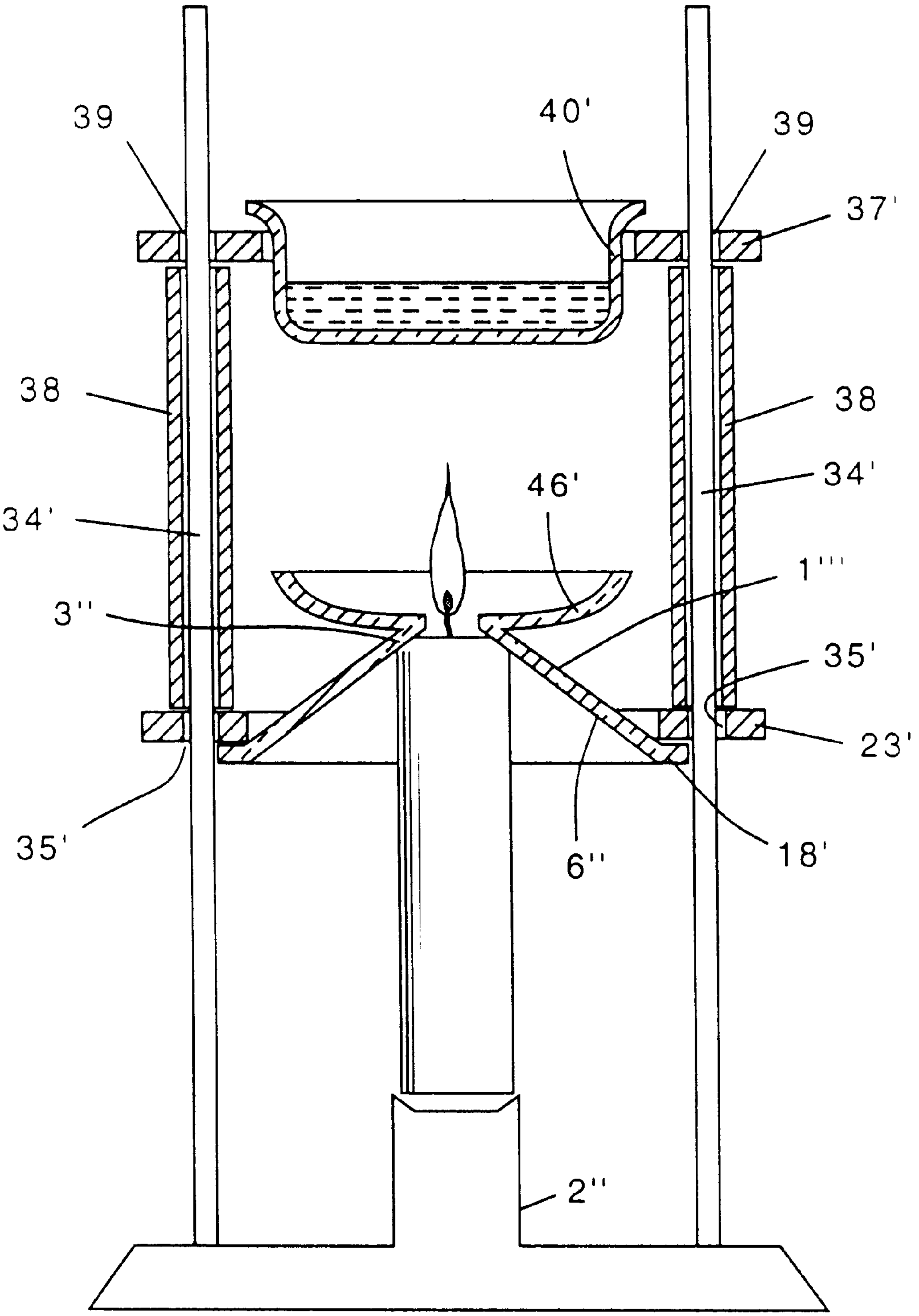
FIG. 5 is an elevational view, partly in cross-section of a fifth embodiment of socketless drip preventing and fragrance dispensing candle holder with the candle partly consumed.

In the fifth embodiment, shown schematically in FIG. 5, the guide rods 34' are anchored in the base of the stand 2" and the rod receiving sockets 35' slidingly receiving respective rods are provided in the metal annulus 23' at opposite diametrical locations. The candle follower or cap 1'" has an extended lip 46', flaring outward and upward to form a melted wax receiving bowl and the shoulder portion 3" and skirt 6" extending radially outwardly in diverging downwardly in their entirety, being continuously conical, terminating in the lower edge portion 18' which extends horizontally, flange fashion, on which the annulus 23' sits. The rods also extend vertically above the cap within spacing sleeves 38 which are supported at lower ends on the annulus 23' providing support rods carrying a further annulus 37' on upper ends having diametrically opposite sockets 39 receiving the upper ends of the rods as a sliding fit. As in the prior embodiment, the further annulus supports a glass bowl 40' of liquid fragrance at a constant height above the candle flame throughout consumption of the candle as the bowl is ultimately carried by the candle follower.

Figure 6:
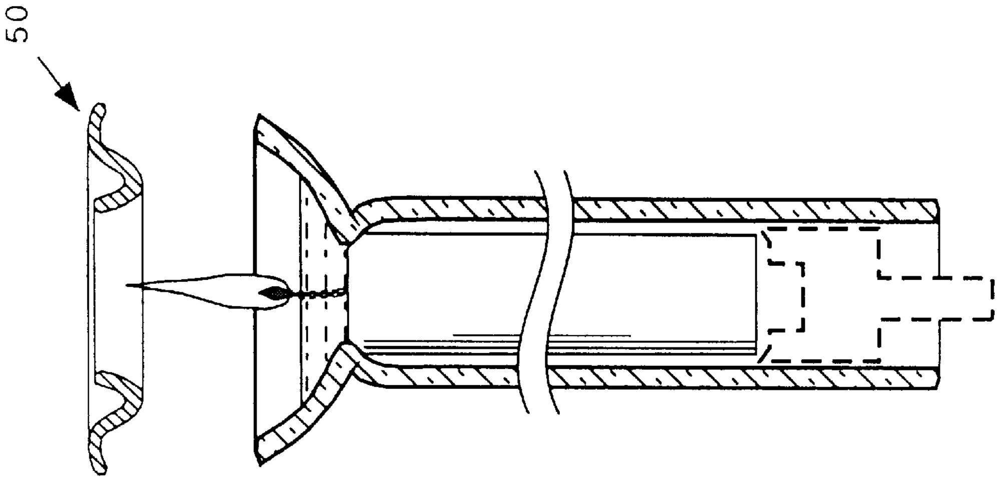
FIG. 6*a* is a schematic, axial cross-sectional view of a sixth embodiment of a combined drip preventing and fragrance dispensing device with the candle partly consumed.
FIG. 6*b* is a similar view to FIG. 6*a* but showing a seventh embodiment with the reservoir raised above the bowl.
Figure 6:
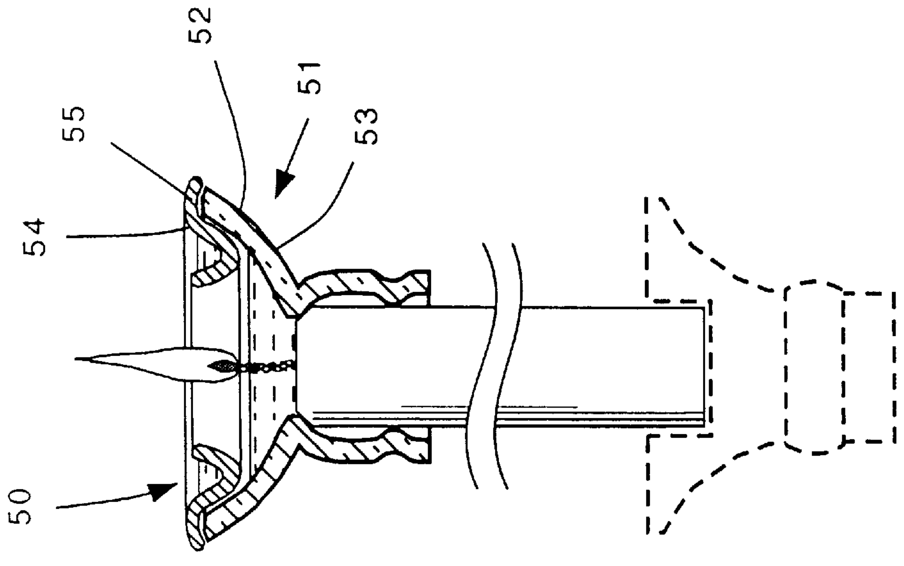

In the sixth embodiment shown in FIG. 6*a*, the candle follower 51 includes a wax receiving bowl 52 formed by an outwardly and upwardly flaring wall 53 and an annular metal dish 54 is formed with an inner, annular, liquid fragrance receiving compartment forming the fragrance reservoir and having a radially outwardly extending flange-like rim 55 which seats around an upper edge of the wall 53 at approximately the height of the flame locating the inner compartment inside the bowl wall so that the heat therefrom is radiated evenly to the inner wall of the dish. Glass would be an alternative material for the reservoir. Vent holes may be provided in the wall 53 of the bowl 52 at locations above the level of molten wax to assure an adequate ventilation for continuous candle burning. A ring of radially inwardly extending, candle engaging, protruberences are formed around the skirt adjacent a lower end thereof to obviate tilting through descent which otherwise could prevent descent of the candle follower.

Figure 7:
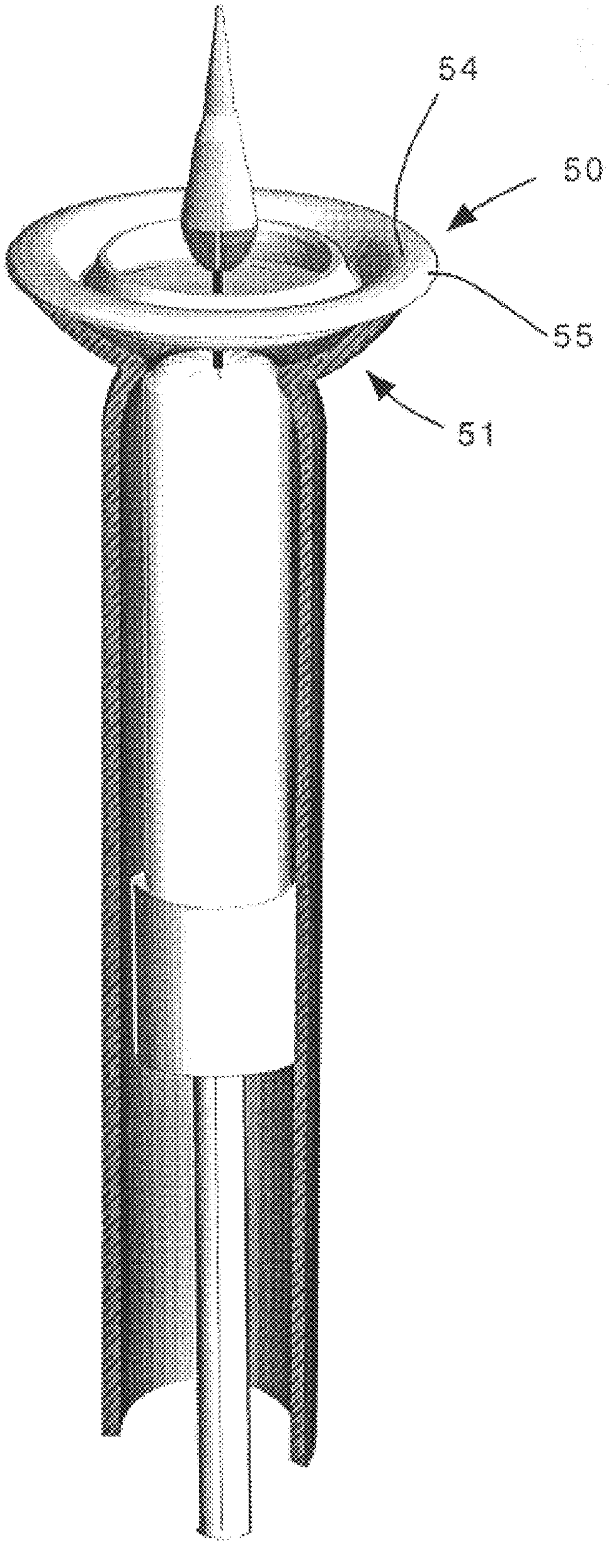
FIG. 7 is a perspective view, partly cut away, of the seventh embodiment; and, FIGS. 8*a* and 8*b* are similar views to FIGS. 6*a* and 6*b*, respectively, of an eight embodiment.

The seventh embodiment of FIGS. 6*b* and 7, is similar to the prior embodiment except that the skirt is longer, extending below the upper end of the top of the candlestick for enhanced guiding and candle holding during descent.

Figure 8:
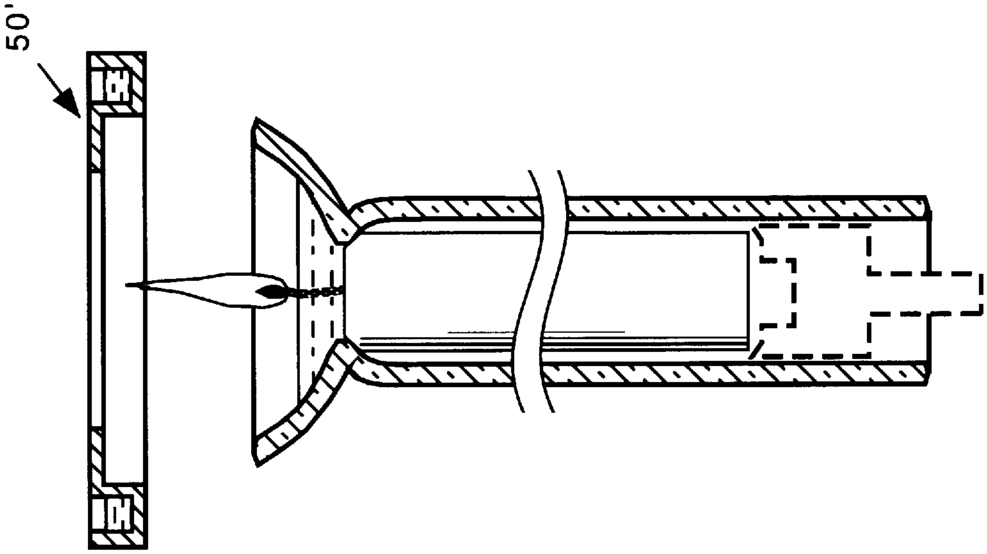
Figure 8:
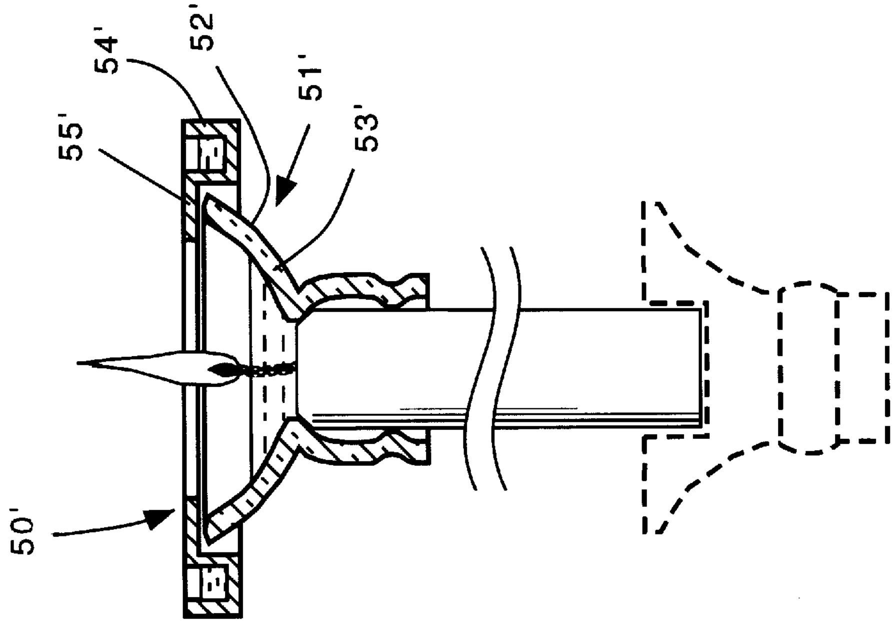

In the eight embodiment of FIGS. 8*a* and 8*b*, the annular dish 54' is formed with annular channel section compartment located outside the bowl wall by a radially inwardly extending rim 55' resting on the upper edge of the wall 53' with the inner edge of the rim sufficiently close to the flame to conduct sufficient vaporizing heat to the reservoir. This may afford additional safety from a flame-over particularly when the liquid fragrance is flammable.

The disclosure of parent application Ser. No. 09/095997, filed Jun. 11, 1998, is incorporated herein by reference.

For the purpose of any divisional design patent application, the candle, candlestick, melted wax and liquid fragrance are solely environmental and do not form part of any design.

I claim:

1. A combined drip preventing and fragrance dispensing device comprising a candle follower of a type having an annular shoulder portion for sitting on a shoulder of the candle to descend under gravity during consumption thereof and a central, wick receiving opening with an annular lip and a cylindrical skirt depending from the annular shoulder portion for receiving a candle body; wherein the candle follower is one piece of transparent material and is formed at an upper end with a bowl flaring outwardly and upwardly from the annular lip comprising an outer wall portion and an inner wall portion joined to the outer wall portion at a location spaced from and above the annular lip, thereby dividing the bowl into inner and outer compartments, for containing, respectively, melted candle wax and volatile fragrance for vaporization by heat from the candle.

2. A combined drip preventing and fragrance dispensing device according to claim 1 wherein the inner wall portion is annular, extending substantially concentrically within the outer wall portion so that the outer compartment for volatile fragrance surrounds the inner compartment.

3. A combined drip preventing and fragrance dispensing device according to claim 1 wherein the outer compartment provides a reservoir for liquid fragrance and the inner wall portion seals the outer compartment liquid tight from the inner compartment.

4. A combined drip preventing and fragrance dispensing device according to claim 2 wherein the outer compartment provides a reservoir for liquid fragrance and the inner wall portion seals the outer compartment liquid tight from the inner compartment.

5. A combined drip preventing and fragrance dispensing device comprising a candle follower of a type having an annular shoulder portion for sitting on a shoulder of the candle to descend under gravity during consumption thereof and a central, wick receiving opening with an annular lip and a cylindrical skirt depending from the annular shoulder portion for receiving a candle body; wherein the candle follower is one piece of transparent material and is formed at an upper end with a bowl flaring outwardly and upwardly from the annular lip comprising an outer wall portion and an inner wall portion joined to the outer wall portion, thereby dividing the bowl into inner and outer compartments, for containing, respectively, melted candle wax and volatile fragrancel for vaporization by heat from the candle, the inner wall portion comprising at least two, semicircular, inner wall parts formed on an inside of the outer wall portion at equal intervals therearound defining therewith respective fragrance containing compartments.

6. A combined drip preventing and fragrance dispensing device according to claim 5 wherein the outer compartments provide reservoirs for liquid fragrance and the inner wall parts seal the respective outer compartments liquid tight from the inner compartment.

7. A combined drip preventing and fragrance dispensing device according to claim 6 wherein the inner wall portion joins the outer wall at a location spaced from and above the annular lip thereof so that the outer compartment is at a higher level than the melted wax and the inner wall portions incline inwardly as they extend upward.

8. A combined drip preventing and fragrance dispensing device comprising a candle follower of a type having an annular shoulder portion for sitting on a shoulder of the candle to descend under gravity during consumption thereof and a central, wick receiving opening with an annular lip and a cylindrical skirt depending from the annular shoulder portion for receiving a candle body; wherein the candle follower is one piece of transparent material and is formed at an upper end with a bowl flaring outwardly and upwardly from the annular lip comprising an outer wall portion and an inner wall portion joined to the outer wall portion, thereby dividing the bowl into inner and outer compartments, for containing, respectively, melted candle wax and volatile fragrance for vaporization by heat from the candle, the outer compartment providing a reservoir for liquid fragrance and the inner wall portion sealing the outer compartment liquid tight from the inner compartment and the inner wall portion joining the outer wall at a location spaced from and above the annular lip thereof so that the outer compartment is at a higher level than the melted wax and the inner wall portion inclines inwardly as it extends upward.

9. A combined drip preventing and fragrance dispensing device comprising a candle follower of a type having an annular shoulder portion for sitting on a shoulder of the candle to descend under gravity during consumption thereof and a central, wick receiving opening with an annular lip and a cylindrical skirt depending from the annular shoulder portion for receiving a candle body; wherein the candle follower is one piece of transparent material and is formed at an upper end with a bowl flaring outwardly and upwardly from the annular lip comprising an outer wall portion and an inner wall portion joined to the outer wall portion, thereby dividing the bowl into inner and outer compartments, for containing, respectively, melted candle wax and volatile fragrance for vaporization by heat from the candle, the inner wall portion being annular, extending substantially concentrically within the outer wall portion so that the outer compartment for volatile fragrance surrounds the inner compartment, the outer compartment providing a reservoir for liquid fragrance and the inner wall portion sealing the outer compartment liquid tight from the inner compartment, the inner wall portion joining the outer wall at a location spaced from and above the annular lip thereof so that the outer compartment is at a higher level than the melted wax and the inner wall portion inclines inwardly as it extends upward.

10. A combined drip preventing and fragrance dispensing device comprising a candle follower of a type having an annular shoulder portion for sitting on a shoulder of the candle to descend under gravity during consumption thereof and a central, wick receiving opening with an annular lip and a cylindrical skirt depending from the annular shoulder portion for receiving a candle body; wherein the candle follower is one piece of transparent material and is formed at an upper end with a bowl flaring outwardly and upwardly from the annular lip comprising an outer wall portion and an inner wall portion joined to the outer wall portion, thereby dividing the bowl into inner and outer compartments, for containing, respectively, melted candle wax and volatile fragrance for vaporization by heat from the candle, further comprising a stand having a base and an upstanding, socketless candlestick with a recessed candle supporting surface, the skirt being elongate for containing an entire candle and so that the candlestick is receivable in sliding engagement within the skirt, guiding descent of the cap member throughout the entire burning of the candle and for sealing engagement within the cap member during a final stage of consumption to prevent leakage of melted wax.

11. A combined drip preventing and fragrance dispensing device comprising a candle follower of the type having an annular shoulder portion for sitting on a shoulder of the candle to descend under gravity during consumption thereof and a central, wick receiving opening with an annular lip and a cylindrical skirt depending from the annular shoulder portion for receiving a candle body; wherein the candle follower carries a reservoir for fragrance for vaporization by heat from the burning candle, the candle follower including a wax receiving bowl formed by a wall which extends outward and upwards from the annular lip and the fragrance reservoir being provided by an annular dish which is removably mounted by the wall to surround the flame.

12. A combined drip preventing and fragrance dispensing device according to claim 11 wherein the dish has a rim which extends radially outwardly and seats on an upper edge of the wall mounting the reservoir between the wall and the flame.

13. A combined drip preventing and fragrance dispensing device according to claim 11 wherein the dish is metal.

14. A combined drip preventing and fragrance dispensing device according to claim 11 wherein the dish is metal and has a radially inwardly extending rim which seats around an upper edge of the wall mounting the reservoir outside the bowl wall and having a radially inner edge extending toward the flame to conduct heat therefrom to the reservoir.

15. A fragrance dispensing device according to claim 11 wherein the annular dish has at least two imperforate, fragrance receiving compartments whereby different fragrances can be heated simultaneously in respective compartments.

16. A combined drip preventing and fragrance dispensing device to comprising a candle follower of the type having an annular shoulder portion for sitting on a shoulder of the candle to descend under gravity during consumption thereof and a central, wick receiving opening with an annular lip and a cylindrical skirt depending from the annular shoulder portion for receiving a candle body; wherein the candle follower carries a reservoir for fragrance for vaporization by heat from the burning candle, and further comprising a stand having a base and an upstanding socket-less candlestick with a shallow, concave candle supporting surface at least as wide as the candle for containing melted wax and receivable in sealing engagement within the candle follower during a final stage of consumption to prevent leakage of melted wax;

complementary candle follower guiding means on the candle follower and stand including metal guide rods extending vertically between the candle follower and the stand on opposite sides of the candle and socket means slidingly receiving the guide rods;

whereby the complementary guiding means maintains the candle follower on a fixed vertical axis throughout gravitation down the candle body during total consumption thereof so that the candle follower retains the candle upright on the candle supporting surface;

at least a lower edge portion of the skirt extends radially outwardly, the candle follower guiding means includes a metal annulus which sits on the lower edge portion of the candle follower to extend around the candle spaced radially outwardly therefrom and carries the metal guide rods in depending relation, the guide rod receiving socket means being located in a lateral bearing member provided on the stand at a sufficient height above the foot to permit full descent of the candle follower and, at a final stage of burning, the candle supporting surface engages the candle follower adjacent the aperture to permit total consumption of the candle;

support rods extending upward from the metal annulus and have upper ends supporting a further annulus which support a reservoir of volatile fragrance over the candle flame for warming thereby, whereby the reservoir is maintained at a constant distance from the candle flame throughout consumption of the candle.

17. A combined drip preventing and fragrance dispensing device according to claim 16, wherein the candle follower is transparent.

18. A combined drip preventing and fragrance dispensing device comprising a candle follower of the type having an annular shoulder portion for sitting on a shoulder of the candle to descend under gravity during consumption thereof and a central, wick receiving opening with an annular lip and a cylindrical skirt depending from the annular shoulder portion for receiving a candle body; wherein the candle follower carries a reservoir for fragrance for vaporization by heat from the burning candle, and further comprising a stand having a base and an upstanding socket-less candlestick with a shallow, concave candle supporting surface at least as wide as the candle for containing melted wax and receivable in sealing engagement within the candle follower during a final stage of consumption to prevent leakage of melted wax;

complementary candle follower guiding means on the candle follower and stand including metal guide rods extending vertically between the candle follower and the stand on opposite sides of the candle and socket means slidingly receiving the guide rods;

whereby the complementary guide means maintains the candle follower on a fixed vertical axis throughout gravitation down the candle body during total consumption thereof so that the candle follower retains the candle upright on the candle supporting surface;

the improvement residing in that at least a lower edge portion of the skirt extends radially outwardly, the guide rods being anchored in the foot of the stand and the candle follower guiding means including a metal annulus which sits on the lower edge portion of the candle follower extending around the candle spaced radially outwardly therefrom and is formed with the guide rod receiving sockets and, at a final stage of burning, the candle supporting surface engages the candle follower adjacent the aperture to permit total consumption of the candle;

support rods extending vertically above the candle follower within metal spacing sleeves which are supported at lower ends on the annulus and carry a further annulus on upper ends having sockets receiving upper ends of the rods as a sliding fit, a reservoir of volatile fragrance being supported by the further annulus over the candle flame for warming thereby, whereby the reservoir is maintained at a constant distance from the candle flame throughout consumption of the candle.

19. A candle holder according to claim 18, wherein substantially the entire skirt diverges radially outwardly while extending downwards.

* * * * *